United States Patent

Wingert et al.

[11] Patent Number: 5,719,171
[45] Date of Patent: Feb. 17, 1998

[54] DIARYL DERIVATIVES AND THEIR USE AS CROP PROTECTION AGENTS

[75] Inventors: Horst Wingert, Mannheim; Beate Hellendahl, Schifferstadt; Hubert Sauter, Mannheim; Gisela Lorenz, Neustadt, all of Germany

[73] Assignee: BASF Aktiengesellschaft, Ludwigshafen, Germany

[21] Appl. No.: 479,453

[22] Filed: Jun. 7, 1995

Related U.S. Application Data

[62] Division of Ser. No. 231,487, Apr. 22, 1994, Pat. No. 5,594,020.

[30] Foreign Application Priority Data

Apr. 23, 1993 [DE] Germany .............. 43 13 267.7

[51] Int. Cl.$^6$ .............................. A01N 43/824
[52] U.S. Cl. .................. 514/363; 514/364; 514/365; 514/367; 514/378
[58] Field of Search ............... 514/378, 364, 514/363, 367, 365

[56] References Cited

U.S. PATENT DOCUMENTS

| | | | |
|---|---|---|---|
| 3,816,443 | 6/1974 | Dorn | 848/169 |
| 3,947,582 | 3/1976 | Shen | 548/189 |
| 5,401,763 | 3/1995 | Camaggi | 514/378 |
| 5,543,433 | 8/1996 | Doetzer | 514/638 |

*Primary Examiner*—Robert Gerstl
*Attorney, Agent, or Firm*—Oblon, Spivak, McClelland, Maier & Neustadt, P.C.

[57] ABSTRACT

Diaryl derivatives of the general formula I

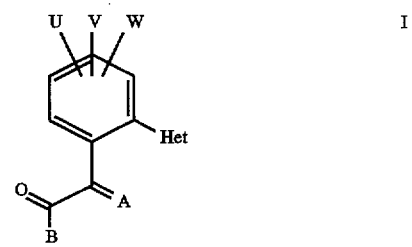

where
A is =CHOR$^1$, =CHSR$^1$, =CHR$^1$, =CHCl or =NOR$^1$,
B is OR$^2$, SR$^2$ or NR$^2$R$^3$ and
Het is a mono-, di- or trinuclear aromatic five- or six-membered heterocyclic structure which is unsubstituted or substituted by R,
R$^1$, R$^2$, R$^3$, R$^4$, R$^5$ are identical or different and each is hydrogen or alkyl, and
U, V, W are identical or different and each is halogen, alkyl or alkoxy, and fungicides containing these compounds.

12 Claims, No Drawings

DIARYL DERIVATIVES AND THEIR USE AS CROP PROTECTION AGENTS

This is a Division of application Ser. No. 08/231,487, filed on Apr. 22, 1994, now U.S. Pat. No. 5,594,020.

The present invention relates to novel diaryl derivatives of the general formula I

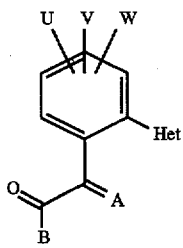

where:

A is =CHOR$^1$, =CHSR$^1$, =CHR$^1$, =CHCl or =NOR$^1$,
B is OR$^2$, SR$^2$ or NR$^2$R$^3$,
Het is a mono-, di- or trinuclear, five- or six-membered heterocyclic structure which may carry from one to three radicals R,
R is halogen, nitro, cyano, CO$_2$R$^4$, NR$^4$R$^5$, CONR$^4$R$^5$, S(O)$_n$R$^4$ P(O)(OR$^4$)$_2$, substituted or unsubstituted C$_1$–C$_6$-alkyl, C$_1$–C$_4$-haloalkyl, substituted or unsubstituted C$_3$–C$_6$-cycloalkyl, C$_1$–C$_4$-alkoxy-C$_1$–C$_4$-alkyl, C$_1$–C$_4$-alkylthio-C$_1$–C$_4$-alkyl, substituted or unsubstituted C$_2$–C$_6$-alkenyl, substituted or unsubstituted C$_2$–C$_6$-alkynyl, C$_1$–C$_6$-alkoxy, C$_1$–C$_4$-thioalkoxy, substituted or unsubstituted benzylthio,
C$_1$–C$_4$-alkylcarbonyl, substituted or unsubstituted phenylcarbonyl, substituted or unsubstituted aryl, substituted or unsubstituted aryloxy, substituted or unsubstituted arylthio, substituted or unsubstituted aryl-C$_1$–C$_4$-alkyl, substituted or unsubstituted aryl-C$_2$–C$_4$-alkenyl, substituted or unsubstituted aryl-C$_2$–C$_4$-alkynyl, substituted or unsubstituted aryloxy-C$_1$–C$_4$-alkyl, substituted or unsubstituted arylthio-C$_1$–C$_4$-alkyl, substituted or unsubstituted hetaryl, substituted or unsubstituted hetaryloxy, substituted or unsubstituted hetaryl-C$_1$–C$_4$-alkyl, substituted or unsubstituted hetaryl-C$_2$–C$_4$-alkenyl, or unsubstituted hetaryloxy-C$_1$–C$_4$-alkyl,
"substituted or unsubstituted" denoting the radicals halogen, cyano, nitro, C$_1$–C$_4$-alkyl, C$_1$–C$_4$-alkoxy, C$_1$–C$_4$-haloalkyl, C$_1$–C$_4$-haloalkoxy or C$_1$–C$_4$-alkoximino-C$_1$–C$_2$-alkyl and
where
n is 0, 1 or 2,
R$^1$, R$^2$, R$^3$, R$^4$, R$^5$ are identical or different and each is hydrogen or C$_1$–C$_4$-alkyl and
U, V, W are identical or different and each is halogen, C$_1$–C$_4$-alkyl or C$_1$–C$_4$-alkoxy, and methods of combatting pests, especially fungi, insects, nematodes and mites, with these compounds.

The use of methyl 2-phenyl-3-methoxyacrylate or phenylglyoxylic acid methyl ester-O-methyloximes substituted in the phenyl moiety at the 2-position by hetarylmethyl, hetarylethenyl, hetaryloxy, phenyl or hetaryloxymethyl as fungicides has been disclosed (EP-A 178 826, EP-A 350 691, EP-A 363 818, EP-A 378 755 and EP-A 254 426). However, their fungicidal action is unsatisfactory.

The object of the invention was to provide novel compounds with improved properties.

We have found that this object is achieved by the novel compounds I. We have further found that the compounds I have an excellent fungicidal, insecticidal, nematicidal and acaricidal action. The fungicidal and insecticidal action is preferred.

The preparation of the compounds of the general formula I is described below:

As an abbreviation for the group

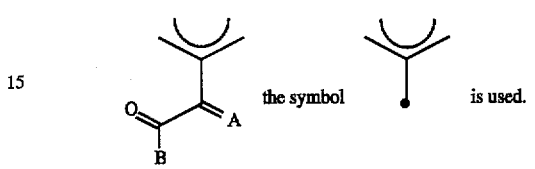

The novel compounds of the general formula Ib can be prepared for instance by reacting, in conventional manner, a bromoaromatic compound of the general formula 1 with a heteroaromatic tin compound 2 or a heteroaromatic boron compound 3 in the presence of a transition metal catalyst (TM), preferably a nickel or palladium compound such as NiCl$_2$, Pd(OAc)$_2$, PdCl$_2$ or Pd(PPh$_3$)$_4$ (see, for example, Synthesis, 693 (1987); T. R. Bailey, Tetrah. Lett. 4407 (1986); Y. Yamamoto, Heterocycles 16,1161 (1981)). The heteroaromatic tin and boron compounds are known or may be prepared analogously to known methods.

Scheme 1

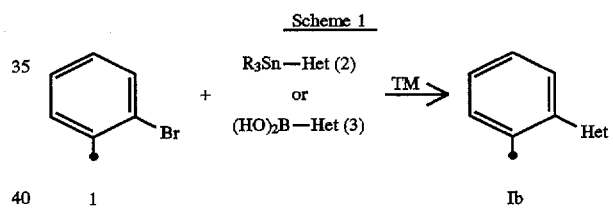

Another way of preparing the compounds of the general formula I, Het denoting an aromatic five-membered heterocyclic structure, is [3+2]-dipolar cycloaddition.

In this way, the acetylene derivatives 4 can be reacted in conventional manner with 1,3-dipoles 5 to give the desired aromatic five-membered heterocyclic structures 6 (see Houben-Weyl, vol. 5/2a, pp. 830 et seq. (1977)).

Scheme 2

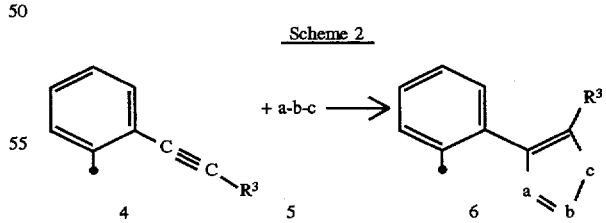

For example the following derivatives may be prepared in this way:

—The isoxazole derivatives 8 and 9 are obtained by reaction of nitrile oxides 7.

Scheme 3

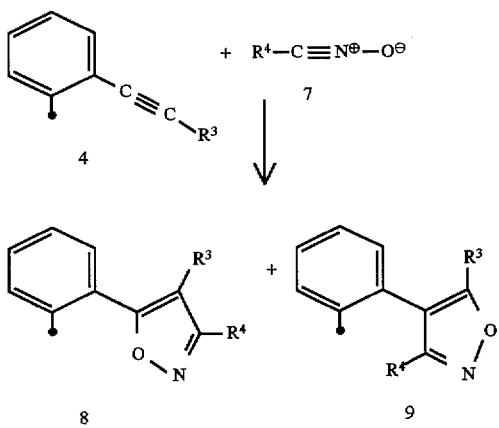

—It is also possible to react an oxime of the general formula 10 with an acetylene 11 in the presence of hypochlorite. The isoxazoles 12 and 13 are obtained.

Scheme 4

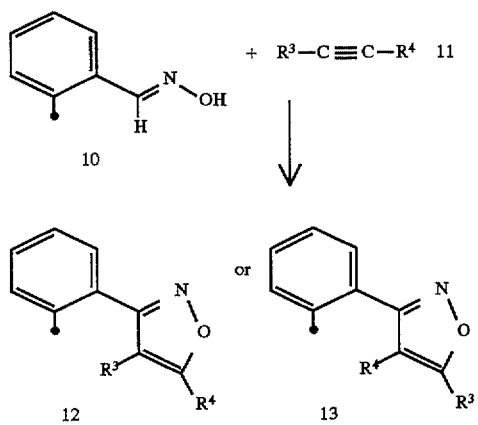

—The triazoles of the general formula 15 may be prepared by reaction of acetylenes 4 with azides 14:

Scheme 5

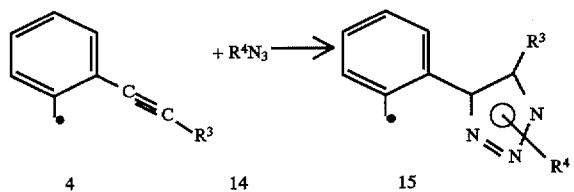

—The pyrroles 17 and 18 may be prepared by reaction of diazoalkanes 16.

Scheme 6

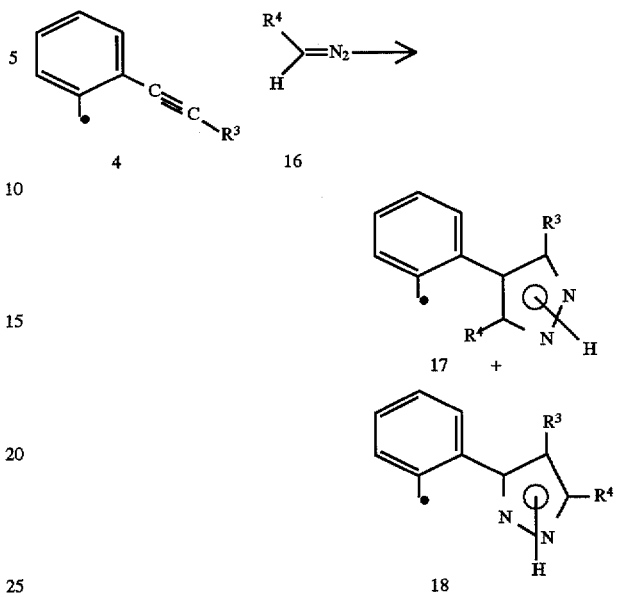

Oxadiazole derivatives 22 may for instance be prepared from acyl-hydrazones 21, which in turn are obtained from aldehydes 19 by reaction with hydrazides 20 (cf. EP 499823).

Scheme 7

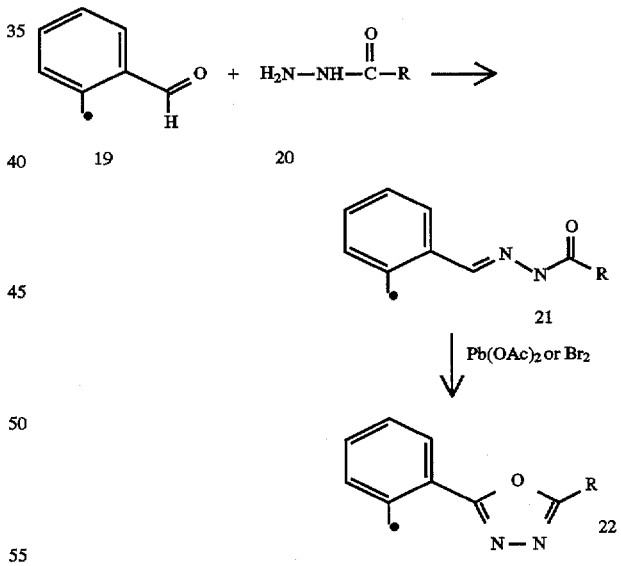

—Oxidation of the hydrazones 21 to the oxadiazoles 22 is carried out for instance with lead tetraacetate or with bromine in a solvent or diluent such as methylene chloride or chloroform (cf. for example Synthesis, 411, 1986).

A further possibility of preparing the novel compounds of the formula I is shown in Scheme 8:

5

Scheme 8

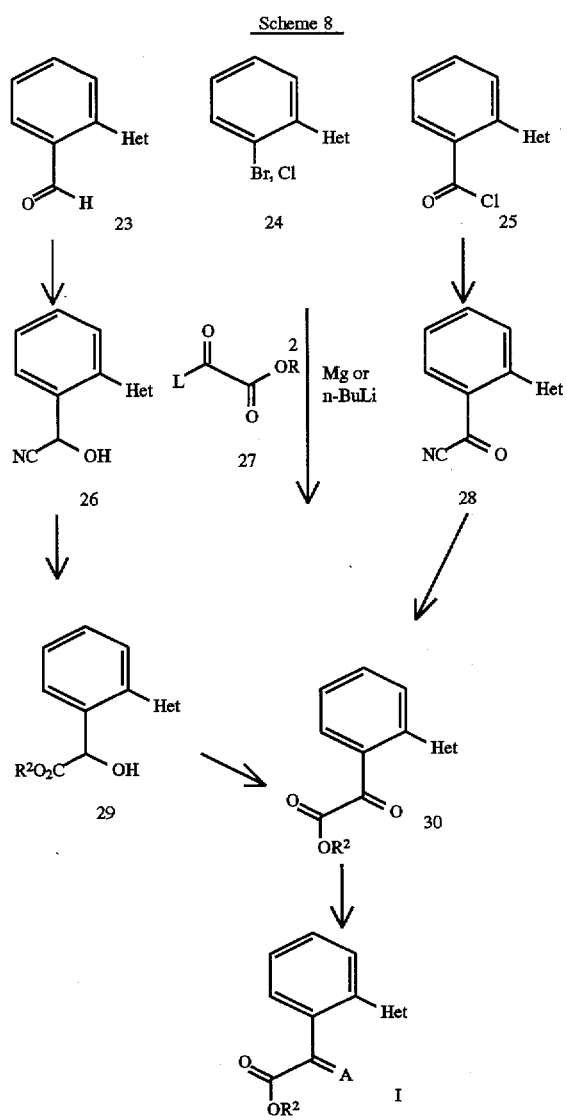

—The aldehydes may be converted in conventional manner via the cyanohydrins 26 into the mandelic acid derivatives 29 (cf. for example U.S. Pat. No. 2,892,847), which can be oxidized to the keto esters 30 analogously to known methods, for example with sodium hypochlorite (cf. for example EP-A 140 454).

—The keto esters 30 may also be prepared in one stage from the halogen derivatives 24 via Grignard or organometallic intermediate stages (cf. for example Synth. Comm. 20, 1781 (1990)).

—A further possibility of preparing the keto esters is to convert the acyl chlorides 25 into the benzoyl cyanides 28, which can then be converted in a Pinner reaction into the keto esters 30 (cf. for example EP-A 493 711).

The esters of the general formula I are obtained from the keto esters 30 prepared in this way by

Scheme 9

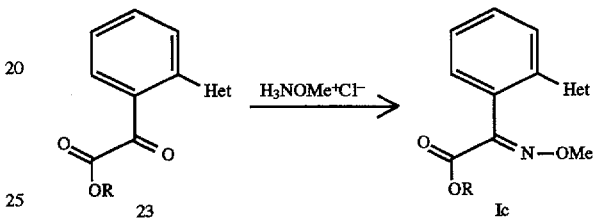

a) converting the keto esters 23 into the oxime ethers Ic with methoxyaminohydrochloride, or

Scheme 10

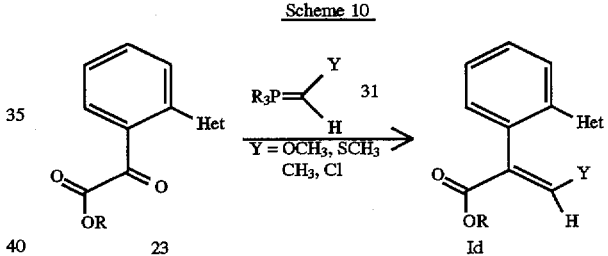

b) by reacting the keto esters 23 with the ylids 31 along the lines of a Wittig or a Wittig-Horner reaction.

The thiol esters or the methylamides may be obtained in conventional manner as follows from the esters Ie prepared in this way:

Scheme 11

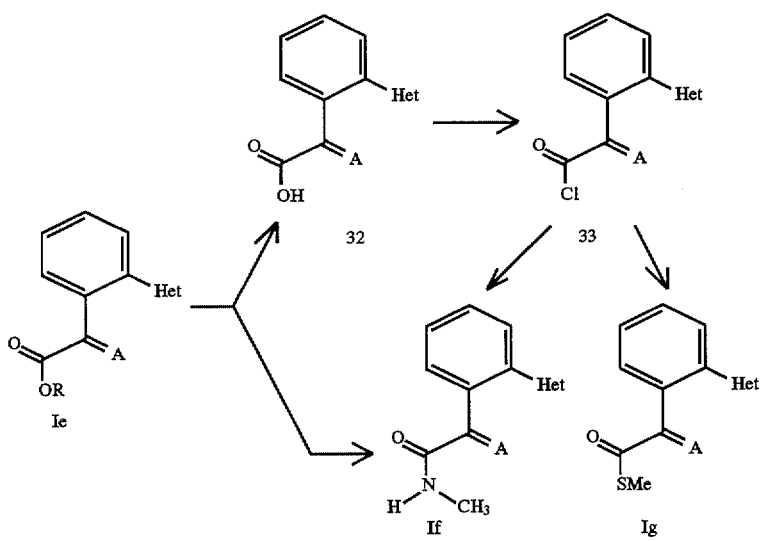

The thiol esters Ig can be obtained in conventional manner via the intermediate compounds acid 32 and acyl chloride 33 (cf. EP-A 432 503).

The methyl amides If may be prepared either directly by aminolysis of the esters Ie (cf. EP-A 477 631) or by aminolysis of the acyl chlorides 33 (EP-A 477 631).

Because of the C=C or C=N double bonds, the novel compounds of the general formula I may be obtained as an E/Z mixture of isomers. These isomers can be separated in conventional manner, e.g., by crystallization or chromatography, into their individual components. Both the individual isomeric compounds and mixtures thereof are encompassed by the invention and can be used as pesticides.

The radicals in the general formula I have for example the following meanings:

A is =$CHOR^1$, =$CHSR^1$, =$CHR^1$, =CHCl or =$NOR^1$,
B is $OR^2$, $SR^2$ or $NR^2R^3$ and the term Het is a mono-, di- or trinuclear aromatic five- or six-membered heterocycle, e.g., pyridyl, pyridazinyl, pyrimidinyl, pyrazinyl, triazinyl, tetrazinyl, quinolinyl, phenazinyl, thienyl, furyl, pyrryl, imidazolyl, oxazolyl, isoxazolyl, thiazolyl, thiadiazolyl, oxadiazolyl, tetrazolyl, benzothienyl, benzofuranyl, indolyl, benzimidazolyl, benzooxazolyl, benzothiazolyl or benzisoxazolyl, which is unsubstituted or substituted by from one to three of the radicals R, where R is identical or different and is hydrogen, halogen (e.g., fluoro, chloro, bromo, iodo), nitro, cyano, $NR^4R^5$, $CO_2R^4$, $CONR^4$, $R^5$, $S(O)_nR^4$ where n=0, 1 or 2, P(O) $(OR^4)_2$, straight-chain or branched $C_1$–$C_{10}$-alkyl (e.g., methyl, ethyl, n- and isopropyl, n-, iso-, sec.-, and tert.-butyl, n-pentyl, neopentyl, n-hexyl, n-decyl ), $C_1$–$C_4$-haloalkyl (e. g., chloromethyl, bromomethyl, fluoromethyl, dichloromethyl, difluoromethyl, trifluoromethyl, 1,2-dibromoethyl, 1,1,2,2-tetrafluoroethyl, pentafluoroethyl ), $C_3$–$C_6$-cycloalkyl (cyclopropyl, 1-methylcyclopropyl, cyclobutyl, cyclopentyl, cyclohexyl), $C_1$–$C_4$-alkoxy-$C_1$–$C_4$-Alkyl (e.g., methoxymethyl, ethoxymethyl, tert. -butoxymethyl, methoxyethyl, ethoxyethyl, butoxyethyl), $C_1$–$C_4$-alkylthio-$C_1$–$C_4$-alkyl (e.g., methylthiomethyl, methylthioethyl), $C_2$–$C_6$-alkenyl (e.g., ethenyl, propen-1-yl, propen-2-yl, propen-3-yl, 2-buten-2-yl), substituted or unsubstituted $C_2$–$C_6$-alkynyl (e.g., ethynyl; methoxyethynyl, propynyl, 3-phenylethyn-1-yl, 3-hydroxypropyn-1-yl, 3-chloropropyn-1-yl), $C_1$–$C_6$-alkoxy (e.g., methoxy, ethoxy, n-and isopropoxy, n-, iso-, sec.-and tert.-butoxy), $C_1$–$C_4$-alkylthio (e.g., methylthio), substituted or unsubstituted benzylthio (e.g., 2-chlorobenzylthio), $C_1$–$C_4$-alkylcarbonyl (e.g., acetyl, ethylcarbonyl, isopropylcarbonyl), substituted or unsubstituted phenylcarbonyl (e.g., 2-chlorophenylcarbonyl, 4-methylphenylcarbonyl), substituted or unsubstituted aryl, phenyl, naphthyl (e.g., 4-methylphenyl, 3-hydroxy-4-methylphenyl, 1-naphthyl, 2-methyl-1-naphthyl), substituted or unsubstituted aryloxy (e.g., phenoxy, 2-methylphenoxy, 4-chlorophenoxy, 3-nitrophenoxy), substituted or unsubstituted arylthio (e.g., phenylthio), substituted or unsubstituted aryl-$C_1$–$C_4$-alkyl ( e. g., benzyl, 2 -chlorobenzyl, 2,5-dimethoxybenzyl, phenethyl, 4-methylphenethyl), substituted or unsubstituted aryl-$C_2$–$C_4$-alkenyl (phenylethenyl, 2-chlorophenylethenyl), substituted or unsubstituted aryl-$C_2$–$C_4$-alkynyl (phenylethinyl, 4-methylphenylethynyl, 2-naphthylethynyl), substituted or unsubstituted aryloxy-$C_1$–$C_4$-alkyl (e.g., phenoxymethyl, 2-CN-phenoxymethyl, 1-naphthyloxymethyl, phenoxyethyl), substituted or unsubstituted arylthio-$C_1$–$C_4$-alkyl (e.g., phenylthiomethyl), substituted or unsubstituted hetaryl (e.g., pyridyl, thienyl, 2-chlorothien-5-yl), substituted or unsubstituted hetaryloxy (e.g., 2-pyridyloxy, 2-benzothienyloxy, 2-benzoxazolyloxy), substituted or unsubstituted hetaryl-$C_1$–$C_4$-alkyl (e.g., 4-pyridylmethyl, 4-chloro-2-thienylmethyl), substituted or unsubstituted hetaryl-$C_2$–$C_4$-alkenyl (e.g., 2-pyridylethenyl, 6-chloro-2-pyridylethenyl, 2-thiazolylethenyl), substituted or unsubstituted hetaryloxy-$C_1$–$C_4$-alkyl (e.g., 2-pyridyloxymethyl, 2-benzoxazolyloxymethyl, 6-methyl-2-benzthiazolyloxymethyl), where "substituted or unsubstituted" means the radicals halogen, cyano, nitro, $C_1$–$C_4$-alkyl (e.g., methyl, ethyl), $C_1$–$C_4$-alkoxy (e.g., methoxy, ethoxy, tert.butoxy), $C_1$–$C_4$-haloalkyl (e.g., trifluoromethyl), $C_1$–$C_4$-haloalkoxy (e.g., trifluoromethoxy, $C_1$–$C_4$-alkoximino-$C_1$–$C_2$-alkyl (e.g., methoximinomethyl, ethoximinomethyl, methoximinoethyl) and the term hetaryl has the above-mentioned meanings, and $R^1$, $R^2$, $R^3$, $R^4$, $R^5$ are identical or different and each is hydrogen or $C_1$–$C_4$-alkyl (e.g., methyl, ethyl, n- or isopropyl, or n-, iso-, sec- or tert. -butyl ) and U, V, W are identical or different and each is hydrogen, halogen, $C_1$–$C_4$-alkyl (e.g., methyl, ethyl, propyl, butyl) or $C_1$–$C_4$-alkoxy (e.g., methoxy, ethoxy ).

Preferred compounds I are those in which A is =CHOCH$_3$ or =NOCH$_3$.

Compounds I in which B is methoxy or methylamino are also preferred.

Further, compounds I in which U, V and W are simultaneously hydrogen are preferred.

Additionally, compounds I are preferred in which Het is a substituted or unsubstituted heterocyclic structure selected from the following group: thiazolyl, benzthiazolyl, isoxazolyl, thiadiazolyl, oxadiazolyl and thienyl.

Particularly preferred compounds I are those in which Her is a substituted or unsubstituted heterocyclic structure selected from the following group: thiazol-2-yl, benzthiazol-2-yl, isoxazol-3-yl, 1,3,4-thiadiazol-2-yl, 1,3,4-oxadiazol-2-yl and thien-2-yl.

Preferred substituents for Het are:

$C_1$–$C_6$-alkyl, which may be partially or completely halogenated (i.e., in which the hydrogen atoms are partially or completely replaced by halogen atoms selected from the group consisting of fluorine, chlorine and/or bromine) , and/or which may bear one of the following radicals: hydroxy, $C_1$–$C_4$-alkoxy, $C_1$–$C_4$-alkylcarbonyloxy, phenyl, naphthyl, phenoxy, naphthyloxy, benzoyloxy, naphthoyloxy or thienyl, and the aromatic groups in turn may bear from one to three of the following radicals: cyano, nitro, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio, $C_3$–$C_8$-cycloalkyl, which may be partially halogenated and/or may bear from one to three of the following groups: $C_1$–$C_4$-alkyl, $C_1$–$C_4$-haloalkyl, $C_1$–$C_4$-alkoxy and $C_1$–$C_4$-haloalkoxy, $C_2$–$C_6$-alkoxy, which may be partially or completely halogenated (i.e., in which the hydrogen atoms are partially or completely replaced by halogen atoms selected from the group consisting of fluorine, chlorine and/or bromine), and/or which may bear one of the following radicals: phenyl, naphthyl, phenoxy, naphthyloxy, benzoyloxy, naphthoyloxy or thienyl, and the aromatic groups in turn may may be partially or completely halogenated and/or may bear from one to three of the following radicals: cyano, nitro, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio, phenyl, imidazolyl, thienyl, benzothienyl and pyridyl, where these groups in turn may be partially or completely halogenated and/or may bear from one to three of the following radicals: cyano, nitro, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio.

Preferred compounds are those in which

A is =CHOCH$_3$ or =NOCH$_3$
B is OCH$_3$ or NHCH$_3$,
U, V, W are hydrogen and
Het, R and $R^4$, $R^5$ have the meanings given above.

The novel compounds of the formula I are suitable as fungicides.

The novel compounds or agents containing them may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

Normally, the plants are sprayed or dusted with the active ingredients or the seeds of the plants are treated with the active ingredients.

Formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene), chlorinated aromatics (e.g., chlorobenzenes), paraffins (e.g., crude oil fractions), alcohols (e.g., methanol, butanol), ketones (e.g., cyclohexanone), amines (e.g., ethanolamine, dimethylformamide), and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as lignin-sulfite waste liquors and methylcellulose.

Examples of surfactants are: alkali metal, alkaline earth metal and ammonium salts of aromatic sulfonic acids, e.g., ligninsulfonic acid, phenolsulfonic acid, naphthalenesulfonic acid and dibutylnaphthalenesulfonic acid, and of fatty acids, alkyl and alkylaryl sulfonates, and alkyl, lauryl ether and fatty alcohol sulfates, and salts of sulfated hexadecanols, heptadecanols, and octadecanols, salts of fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acids, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain meals, bark meal, wood meal, and nutshell meal, cellulosic powders, etc.

Examples of formulations are given below.

I. A solution of 90 parts by weight of a compound according to the invention and 10 parts by weight of N-methyl-d-pyrrolidone, which is suitable for application in the form of very fine drops.

II. A mixture of 20 parts by weight of a compound according to the invention, 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By finely dispersing the solution in water, a dispersion is obtained.

III. An aqueous dispersion of 20 parts by weight of a compound according to the invention, 40 parts by weight of cyclohexanone, 30 parts by weight of isobutanol, 20 parts by weight of the adduct of 40 moles of ethylene oxide and 1 mole of castor oil.

IV. An aqueous dispersion of 20 parts by weight of a compound according to the invention, 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil.

V. A hammer-milled mixture of 80 parts by weight of a compound according to the invention, 3 parts by weight of the sodium salt of diisobutylnaphthalene-α-sulfonic acid, 10 parts by weight of the sodium salt of a ligninsulfonic acid obtained from a sulfite waste liquor, and 7 parts by weight of powdered silica gel. By finely dispersing the mixture in water, a spray liquor is obtained.

VI. An intimate mixture of 3 parts by weight of a compound according to the invention and 97 parts by weight of particulate kaolin. The dust contains 3 wt % of the active ingredient.

VII. An intimate mixture of 30 parts by weight of a compound according to the invention, 92 parts by weight of powdered silica gel and 8 parts by weight of paraffin oil sprayed onto the surface of this silica gel. This formulation of the active ingredient exhibits good adherence.

VIII. A stable aqueous dispersion of 40 parts by weight of a compound according to the invention, 10 parts of the sodium salt of a phenolsulfonic acid-urea-formaldehyde condensate, 2 parts of silica gel and 48 parts of water, which dispersion can be further diluted.

IX. A stable oily dispersion of 20 parts by weight of a compound according to the invention, 2 parts by weight of the calcium salt of dodecylbenzenesulfonic acid, 8 parts by weight of a fatty alcohol polyglycol ether, 20 parts by weight of the sodium salt of a phenolsulfonic acid-urea-formaldehyde condensate and 68 parts by weight of a paraffinic mineral oil.

The novel compounds are extremely effective on a broad spectrum of phytopathogenic fungi, in particular those from the class consisting of the Ascomycetes and Basidiomycetes. Some of them have a systemic action and may be used as foliar and soil fungicides.

The compounds are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits.

The compounds are applied by treating the seeds, plants, materials or soil to be protected against fungus attack with a fungicidally effective amount of the active ingredients.

The compounds may be applied before or after infection of the materials, plants or seeds by the fungi.

The novel compounds are particularly useful for controlling the following plant diseases:

*Erysiphe graminis* in cereals,
*Erysiphe cichoracearum* and *Sphaerotheca fuliginea* in cucurbits,
*Podosphaera leucotricha* in apples,
*Uncinula necator* in vines,
*Puccinia species* in cereals,
*Rhizoctonia solani* in cotton,
*Ustilago species* in cereals and sugar cane,
*Venturia inaequalis* (scab) in apples,
*Helminthosporium species* in cereals,
*Septoria nodorum* in wheat,
*Botrytis cinerea* (gray mold) in strawberries and grapes,
*Cercospora arachidicola* in groundnuts,
*Pseudocercosporella herpotrichoides* in wheat and barley,
*Pyricularia oryzae* in rice,
*Phytophthora infestans* in potatoes and tomatoes,
*Fusarium and Verticillium species* in various plants,
*Plasmopara viticola* in grapes,
*Alternaria species* in fruit and vegetables.

The novel compositions may also be used for protecting materials (timber), for example against *Paecilomyces variotii*.

The fungicidal agents generally contain from 0.1 to 95, and preferably from 0.5 to 90, wt % of active ingredient.

The application rates depend on the type of effect desired, but are generally from 0.02 to 3 kg of active ingredient composition per hectare.

When the compositions are used for treating seed, application rates of from 0.001 to 50, and preferably from 0.01 to 10, g per kg of seed are generally required.

In these application forms, the agents according to the invention may also be present together with other active ingredients, for example herbicides, insecticides, growth regulators, and other fungicides, and may furthermore be mixed and applied together with fertilizers. Admixture with other fungicides frequently results in a greater fungicidal action spectrum.

The following list of fungicides with which the novel compounds may be combined is intended to illustrate possible combinations but not to impose any restrictions.

Examples of fungicides which may be combined with the novel compounds are:
sulfur,
dithiocarbamates and their derivatives, such as
ferric dimethyldithiocarbamate,
zinc dimethyldithiocarbamate,
zinc ethylenebisdithiocarbamate,
manganese ethylenebisdithiocarbamate,
manganese zinc ethylenediaminebisdithiocarbamate,
tetramethylthiuram disulfides,
ammonia complex of zinc N,N'-ethylenebisdithiocarbamate,
ammonia complex of zinc N,N'-propylenebisdithiocarbamate,
zinc N,N'-propylenebisdithiocarbamate and
N,N'-polypropylenebis(thiocarbamyl) disulfide;
nitro derivatives, such as
dinitro(1-methylheptyl)-phenyl crotonate,
2-sec-butyl-4,6-dinitrophenyl 3,3-dimethylacrylate,
2-sec-butyl-4,6-dinitrophenyl isopropylcarbonate and
diisopropyl 5-nitroisophthalate;
heterocyclic substances, such as
2-heptadecylimidazol-2-yl acetate,
2,4-dichloro-6-(o-chloroanilino)-s-triazine,
O,O-diethyl phthalimidophosphonothioate,
5-amino-1-[-bis-(dimethylamino)-phosphinyl]-3-phenyl-1,2,4-triazole,
2,3-dicyano-1,4-dithioanthraquinone,
2-thio-1,3-dithio[4,5-b]quinoxaline,
methyl 1-(butylcarbamyl)-2-benzimidazolecarbamate,
2-methoxycarbonylaminobenzimidazole,
2-(fur-2-yl)-benzimidazole,
2-(thiazol-4-yl)benzimidazole,
N-(1,1,2,2-tetrachloroethylthio)-tetrahydrophthalimide,
N-trichloromethylthiotetrahydrophthalimide, N-trichloromethylthiophthalimide,
N-dichlorofluoromethylthio-N',N'-dimethyl-N-phenylsulfuric acid diamide,
5-ethoxy-3-trichloromethyl-1,2,3-thiadiazole,
2-thiocyanatomethylthiobenzothiazole,
1,4-dichloro-2,5-dimethoxybenzene,
4-(2-chlorophenylhydrazono)-3-methyl-5-isoxazolone,
2-thiopyridine 1-oxide,
8-hydroxyquinoline and its copper salt,
2,3-dihydro-5-carboxanilido-6-methyl-1,4-oxathiyne,
2,3-dihydro-5-carboxanilido-6-methyl-1,4-oxathiyne 4,4-dioxide,
2-methyl-5,6-dihydro-4H-pyran-3-carboxanilide,
2-methylfuran-3-carboxanilide,
2,5-dimethylfuran-3-carboxanilide,
2,4,5-trimethylfuran-3-carboxanilide,
2,5-dimethyl-N-cyclohexylfuran-3-carboxamide,
N-cyclohexyl-N-methoxy-2,5-diethylfuran-3-carboxamide,
2-methylbenzanilide,
2-iodobenzanilide,
N-formyl-N-morpholine-2,2,2-trichloroethylacetal,
piperazine-1,4-diylbis-(1-(2,2,2-trichloroethyl)-formamide),
1-(3,4-dichloroanilino)-1-formylamino-2,2,2-trichloroethane,
2,6-dimethyl-N-tridecylmorpholine and its salts,
2,6-dimethyl-N-cyclododecylmorpholine and its salts,
N[3-(p-tert.-butylphenyl)-2-methylpropyl]-cis-2,6-dimethylmorlpholine,
N-3-(p-tert.-butylphenyl)-2-methylpropyl'-piperidine,
1-2-(2,4-dichlorophenyl)-4-ethyl-1,3-dioxolan-2-yl-ethyl'-1H-1,2,4-triazole,
1-[2-(2,4-dichlorophenyl)-4-n-propyl-1,3-dioxolan-2-yl-ethyl]-1H-1,2,4-triazole,
N-(n-propyl)-N-(2,4,6-trichlorophenoxyethyl)-N'-imidazolyl-urea,
1-(4-chlorophenoxy)-3,3-dimethyl-1-(1H-1,2,4-tri-azol-1-yl)butan-2-one,
1-(4-chlorophenoxy)-3,3-dimethyl-1-(1H-1, 2,4-triazol-1-yl)butan-2-ol,
α-(2-chlorophenyl)-α-(4-chlorophenyl)-5-pyrimidinemethanol,
5-butyl-(2-dimethylamino-4-hydroxy-6-methylpyrimidine,
bis-(p-chlorophenyl)-3-pyridinemethanol,
1,2-bis-(3-ethoxycarbonyl-2-thioureido)-benzene,
1,2-bis-(3-methoxycarbonyl-2-thioureido)-benzene,
and various fungicides, such as
dodecylguanidine acetate,
3-[3-(3,5-dimethyl-2-oxycyclohexyl)-2-hydroxyethyl]-glutaramide,
hexachlorobenzene,
DL-methyl-N-(2,6-dimethylphenyl)-N-fur-2-yl alanate,
methyl DL-N-(2,6-dimethylphenyl)-N-(2'-methoxyacetyl)-alan-ate,
N-(2,6-dimethylphenyl)-N-chloroacetyl-DL-2-aminobutyrolactone,
methyl DL-N-(2,6-dimethylphenyl)-N-(phenylacetyl)-alanate,
5-methyl-5-vinyl-3-(3,5-dichlorophenyl)-2,4-dioxo-1,3-oxazolidine,
3-[3,5-dichlorophenyl]-5-methyl-5-methoxymethyl-1,3-oxazolidine-2,4-dione,
3-(3,5-dichlorophenyl)-1-isopropylcarbamylhydantoin,
N-(3,5-dichlorophenyl)-1,2-dimethylcyclopropane-1,2-dicarboximide,
2-cyano-[N-(ethylaminocarbonyl)-2-methoximino]-acetamide,
1-[2-(2,4-dichlorophenyl)-pentyl]-1H-1,2,4-triazole,
2,4-difluoro-α-(1H-1,2,4-triazol-1-ylmethyl)-benzhydryl alcohol,
N-(3-chloro-2,6-dinitro-4-trifluoromethylphenyl)-5-trifluoromethyl-3-chloro-2-aminopyridine, and
1-((bis-(4-fluorophenyl)-methylsilyl)-methyl)-1H-1,2,4-triazole.

SYNTHESIS EXAMPLES

The directions given in the synthesis examples below were used, after appropriate modification of the starting materials, to obtain further compounds I. The compounds thus obtained are given in the tables below together with their physical data.

Example 1 o-Formylphenylglyoxylic Acid Methyl ester-O-methyloxime (Compound A)

32 g (0.236 mol) of N-methylmorpholine-N-oxi.$H_2O$ 20 g is added to a solution of 20 g (0.07 mol) of 2-bromomethylphenylglyoxylic acid methyl ester-O-methyloxime in 300 ml of $CCl_4$. The mixture is refluxed for 4 hours and then allowed to cool. It is washed with water and 10% strength hydrochloric acid, dried and evaporated down. After chromatography on silica gel using cyclohexane/ethyl acetate there remains 9.5 g (61% of aldehyde (A) as a colorless solid.

$^1$H-NMR (CDCl$_3$/TMS): δ=3.86, 4.01 (s,3H), 7.32–7.93 (m,4H), 9.88 ppm (s,1H).

Example 2

2-(Formylhydroxylamino)phenylglyoxylic Acid Methyl Ester-O-methyloxime (Compound B)

At 60°–70° C., 10 g (45 mmol) of aldehyde A is added in portions to a solution of 7.15 g (67.5 mmol) of $Na_2CO_3$ and 4.7 g (67.5 mmol) of hydroxylamine hydrochloride in 50 ml of isopropanol. After all has been added, the mixture is allowed to cool and is stirred overnight at room temperature. The mixture is evaporated down, and the residue is taken up in ethyl acetate, washed with water, dried and evaporated down. After chromatography using cyclohexane/ethyl acetate there remains 7.5 g (71%) of oxime (B).

$^1$H-NMR (CDCl$_3$/TMS):δ=3.86, 4.03 (s,3H), 7.20–7.68 (m, 4H), 8.00 (s,1H), 8.34 ppm (br, 1H).

Example 3

2-Hydroxylcarbonylphenylglyoxylic Acid Methyl Ester-O-methyloxime (Compound C)

A mixture of 10 g (45 mmol) of compound A, 5.5 g (55 mmol) of chromium trioxide and 100 ml of conc. acetic acid is stirred at 50° C. for 2 hours. The mixture is allowed to cool, and is then diluted with water, extracted with ethyl acetate, dried and evaporated down. There remains 9.9 g (92.5%) of benzoic acid C as an oil.

$^1$H-NMR (DMSO-d$^6$): δ=3.70, 3.89 (s,3H), 7.28–7.89 (m,4H), 12.8 ppm (br, 1H).

Example 4

2-Chlorocarbonylphenylglyoxylic Acid Methyl Ester-O-methyloxime (Compound D)

At –10° to 0° C., 1.1 g (9.3 mmol) of thionyl chloride is dripped into a solution of 2 g (8.43 mmol) of benzoic acid C and 1.3 g (16.40 mmol) of pyridine in 20 ml-of methyl-tert.-butyl ether and 10 ml of methylene chloride. The mixture is allowed to warm up to room temperature and is then stirred overnight at room temperature ($R_7$). The solvent is then removed under reduced pressure. The crude product can be used in this form for further reactions.

Example 5

2-Bromophenylglyoxylic Acid Methyl Ester-O-methyloxime (Compound E)

5.2 g (62 mmol) of O-methylhydroxylamine hydrochloride is added to a solution of 10 g (41 mmol) of methyl 2-bromophenylglyoxylate in 30 ml of methanol, and the mixture is refluxed for 2 hours. The mixture is evaporated down, and the residue is taken up in ethyl acetate and washed with water. After drying and evaporating down, there remains 6.9 g (62%) of compound E.

$^1$H-NMR (CDCl$_3$/TMS) δ=3.88, 4.07 (s,3H), 7.17–7.61 ppm (m,4H).

Example 6

2-Ethynylphenylglyoxylic Acid Methyl Ester-O-methyloxime (Compound F)

33.3 g (0.35 mol) of trimethylsilylacetylene, 3.8 g of palladium(II) acetate, 3.2 g of copper(I) iodide and 8.9 g of triphenylphosphine are added to a solution of 55.4 g (0.23 mol) of methyl 2-bromophenylglyoxylate in 415 ml of triethylamine, and nitrogen is passed through the solution for 30 minutes. The reaction mixture is then heated for 45 minutes at 90° C. The mixture is cooled and filtered. The filtrate is evaporated down, taken up in ethyl acetate and washed with water. The organic phase is dried and evaporated down. There remains 56.8 g of the α-keto ester as a black oil.

The crude product prepared in this way is dissolved in 50 ml of methanol, 38.9 g (0.37 mol) of O-methylhydroxylamine hydrochloride is added and the mixture is heated for 15 minutes at 60° C. The mixture is evaporated down, and the residue is taken up in ethyl acetate and washed with water. The organic phase is dried and evaporated down. There remains 52.4 g of the trimethylsilyl compound as a black oil.

$^1$H-NMR (CDCl$_3$/TMS): δ=0.22 (s,9H, SiMe$_3$); 3.86; 4.06 (s,3H,OCH$_3$); 7.25–7.61 ppm (m, 4H,aryl).

The trimethylsilylacetylene compound prepared in this way is dissolved in 320 ml of methanol and stirred with 3.2 g of potassium carbonate for 1 hour at room temperature (20° C.). The mixture is evaporated down, and the residue is taken up in methylene chloride and washed with 10% strength sodium bicarbonate solution. The organic phase is dried and evaporated down. There remains 36 g (72%, based on methyl 2-bromophenylglyoxylate) of compound F as a black solid.

$^1$H-NMR (CDCl$_3$/TMS): δ=3.17 (s,3H,≡C—H); 3.87; 4.07 (s,3H,OCH$_3$); 7.27–7.60 ppm (m, 4H,aryl).

Example 7

2(5-Phenylisoxazol-3-yl)-Phenylglyoxylic Acid Methyl Ester-O-methyloxime (Compound 37, Tab. I)

5.7 g (7.6 mmol) of sodium hypochlorite and 3 drops of dilute NaOH are added to 700 mg (7.6 mmol) of phenylacetylene and 1.2 g (5 mmol) of compound B in 20 ml of methylene chloride, and the mixture is stirred overnight at room temperature. The methylene chloride phase is separated off and evaporated down. After chromatography on silica gel using cyclohexane/ethyl acetate, there is obtained 700 mg (42%) of compound 37, Tab. I, as an oil.

$^1$H-NMR (CDCl$_3$/TMS): δ=3.80, 4.01 (s,3H), 6.67 (s,2H), 7.35–7.80 ppm (m, 9H).

Example 8

2[3-(2-Methylphenyl)-isoxazol-5-yl]-phenylglyoxylic Acid Methyl Ester-O-methyloxime (Compound 38, Tab. I)

4.5 g of sodium hypochlorite is added to 1 g (3.15 mmol) of compound F and 600 mg (4.73 mmol) of 2-methylbenzaldehyde oxime in 50 ml of methylene chloride, and the whole is stirred for 1 hour at room temperature. The organic phase is separated off, dried and evaporated down. After chromatography on silica gel there is obtained 1 g of compound 38, Tab. I, as an oil.

$^1$H-NMR (CDCl$_3$/TMS): δ=2.48, 3.79, 4.02 (S,3H), 6.52 (S,1H), 7.26–7.94 ppm (8H).

Example 9

2[5-(3-Methylphenyl)-1,3,4-oxadiazol-2-yl]-phenylglyoxylic Acid Methyl Ester-O-methyloxime (Compound 50, Tab. I)

a) 2 g (13.6 mmol) of 3-methylphenylhydrazone is added to a solution of 3 g (13.6 mmol) of compound A in 100 ml of methanol, and the whole is stirred overnight at room temperature. The precipitated solid is suction filtered, washed with diisopropyl ether and dried under reduced pressure. There is obtained 3.6 g (75%) of the iminohydrazone as a solid. M.p.: 231°–232° C.

b) 4.2 g (9.5 mmol) of lead tetraacetate is added to a solution of 1.6 g (4.5 mmol) of the iminohydrazone compound prepared under a) in 100 ml of chloroform, and the whole is stirred overnight at room temperature. 750 ml of water is added, and the organic phase is separated off, dried and evaporated down. There remains 1.5 g (95%) of compound 50, Tab. I, as a solid. M.p.: 166°–167° C.

Example 10

2(Thiazol-2-yl)phenylglyoxylic Acid Methyl Ester-O-methyloxime (Compound 1, Tab. I)

Under a nitrogen blanket, 1.7 g of 2-triethylstannylthiazole is added to a mixture of 1.4 g (5.19 mmol) of the bromo compound (Compound E), 100 mg of palladium(II) chloride and 310 mg of triphenylphosphine in 30 ml of tetrahydrofuran, and the whole is refluxed for 2 hours. The mixture is then filtered and evaporated down. After chromatography on silica gel using cyclohexane/ethyl acetate there remains 700 mg (49%) of compound 1, Tab. I, as an oil.

$^1$H-NMR (CDCl$_3$/TMS) δ=3.75, 3.97 (s,3H), 7.28–7.86 ppm (m, 6H).

Example 11

2[5-Cyclohexyl-1,3,4-thiadiazol-2-yl]-phenylglyoxylic Acid Methyl Ester-O-methyloxime (Compound 48, Tab. I)

At 0° C. 3.6 g of methyl dithiocyclohexanecarboxylate in 25 ml of methanol is added to a solution of 2.1 g of hydrazine hydrate in 7 ml of water. The mixture is stirred for 10 minutes and is then poured into 100 ml of water. It is then neutralized with 10% strength hydrochloric acid, extracted with methyl tert.-butyl ether, dried and evaporated down. The residue is taken up in 50 ml of acetonitrile. At 0° C. a solution of 5.5 g (23 mmol) of compound D in 30 ml of acetonitrile is dripped in, and the mixture is refluxed for 2 hours. Methylene chloride is then added, and the mixture is washed with saturated NaHCO₃ solution and with water, dried and evaporated down.

After chromatography on silica gel using cyclohexane/ethyl acetate there remains 3.5 g (49%) of compound 48, Tab. I, as an oil.

¹H-NMR (CDCl₃/TMS) δ=1.26–3.21 (m, 11H), 3.81, 3.96 (s,3H) 7.30–7.81 ppm (m, 4H).

Example 12

2[Benzthiazol-2-yl]-phenylglyoxylic Acid Methyl Ester-O-methyloxime (Compound 2, Tab. I)

a) Under a nitrogen blanket and at −78° C., 1.5 equivalents of n-BuLi is dripped into a solution of 2 g (6.9 mmol) of 2-Benzthiazol-2-yl-bromobenzene in 20 ml of THF. The mixture is stirred for 1 hour at this temperature, after which 1.6 g of dimethyl oxalate in 20 ml of THF is added. The mixture is allowed to warm up, water is added and the mixture is extracted with methyl tert-butyl ether. After chromatography on silica gel using hexane/methyl tert.-butyl ether there remains 300 mg (15%) of the corresponding phenyl keto ester.
¹H-NMR (CDCl₃/TMS): δ=3.56 (s,3H), 7.38–8.01 ppm (m, 8H).

b) 1 g of methoxyamine hydrochloride is added to a solution of the keto ester prepared in this way in 5 ml of methanol. The mixture is stirred for 1 hour and evaporated down. Chromatography on silica gel using hexane/methyl tert.-butyl ether gives 100 mg of compound 2, Tab. I, as a gray solid.

¹H-NMR (CDCl₃/TMS): δ=3.76, 3.99 (s,3H), 7.35–8.03 ppm (m, 8H).

TABLE I

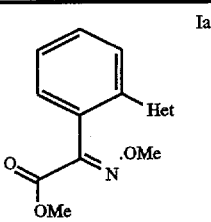

Ia

| No. | Het | Phys. data; H-NMR [δ, ppm], IR[cm⁻¹]; m.p. [°C.] |
|---|---|---|
| 1 | Thiazol-2-yl | 3.75; 3.97(s, 3H); 7.28–7.86(m, 6H) |
| 2 | Benzthiazol-2-yl | 3.76; 3.99(s, 3H); 7.35–8.03(m, 8H) |
| 3 | Thien-2-yl | |
| 4 | Benzthien-2-yl | |
| 5 | Furan-2-yl | |
| 6 | Furan-3-yl | |
| 7 | Benzofuran-2-yl | |
| 8 | Benzofuran-3-yl | |
| 9 | Imidazol-2-yl | |
| 10 | Benzimidazol-2-yl | |
| 11 | Pyrrol-2-yl | |
| 12 | N-Methyl-pyrrol-2-yl | |
| 13 | Pyridin-2-yl | |
| 14 | Pyridin-3-yl | |
| 15 | Pyridin-4-yl | |
| 16 | Quinolin-2-yl | |
| 17 | 6-Chloropyridin-2-yl | |
| 18 | 4-Methyl-pyridin-2-yl | |
| 19 | Oxazol-2-yl | |
| 20 | Benzoxazol-2-yl | |
| 21 | 4-Phenyl-oxazol-2-yl | |
| 22 | 5-Phenyl-oxazol-2-yl | |
| 23 | 5-Methyl-isoxazol-3-yl | |
| 24 | 5-Bromomethyl-isoxazol-3-yl | 3.81; 3.99(s, 3H); 4.48(s, 2H); 6.45; (s, 1H); 7.32–7.71(m, 4H) |
| 25 | 5-Hydroxymethyl-isoxazol-3-yl | 3490, 1717, 1370, 1255, 1081, 1068, 1023, 953, 778 |
| 26 | 5-Acyloxymethyl-isoxazol-3-yl | 2.13; 3.81; 3.99(s, 3H); 5.18(s, 2H); 6.47(s, 1H); 7.32–7.71(m, 4H) |
| 27 | 5-(2-Methyl)phenyloxymethyl-isoxazol-3-yl | 2.25; 3.77; 3.95(s, 3H); 5.14(s, 2H); 6.47(s, 1H); 6.84–7.70(m, 8H) |
| 28 | 5-(2,5-Dimethyl)phenyloxymethyl-isoxazol-3-yl | 2.20; 2.32; 3.77; 3.96(s, 3H); 5.14(s, 2H); 6.47(s, 1H); 6.67–7.71(m, 7H) |
| 29 | 5-tert.-Butyl-isoxazol-3-yl | 1.36(s, 9H); 3.77; 3.96(s, 3H); 6.09(s, 1H); 7.30–7.70(m, 4H) |
| 30 | 5-Cyclohexyl-isoxazol-3-yl | 1.13–2.85(m, 11H); 3.78; 3.99 (s, 3H); 6.11(s, 1H); 7.30–7.71 (m, 4H) |
| 31 | 5-Pentyl-isoxazol-3-yl | 0.71–2.75(m, 11H); 3.79; 4.00 (s, 3H); 6.11(s, 1H); 7.30–7.71 (m, 4H) |
| 32 | 5-[1-(4-Nitrophenoxy)ethyl]-isoxazol-3-yl | 1.80(d, 3H); 3.76; 3.94(s, 3H); 5.60(q, 1H); 6.37(s, 1H); 6.97–8.21(m, 8H) |
| 33 | 5-Benzoyloxymethyl-isoxazol-3-yl | 3.79; 3.97(s, 3H); 5.43(s, 2H); 6.54(s, 1H); 7.28–8.08(m, 9H) |
| 34 | 5-β-Naphthyloxymethylisoxazol-3-yl | 3.74; 3.92(s, 3H); 5.25(s, 2H); 6.53(s, 1H); 7.18–7.78(m, 11H) |
| 35 | 5-α-Naphthyloxymethylisoxazol-3-yl | 3.77; 3.96(s, 3H); 5.35(s, 2H); 6.57(s, 1H); 6.85–8.28(m, 11H) |
| 36 | 5-Thiophenylmethylisoxazol-3-yl | 3.75; 3.93(s, 3H); 4.13(s, 2H); 6.22(s, 1H); 7.20–7.63(m, 9H) |
| 37 | 5-Phenyl-isoxazol-3-yl | 3.80; 4.01(s, 3H); 6.67(s, 1H); 7.35–7.80(m, 9H) |
| 38 | 3-(2-Methyl)phenyl-isoxazol-5-yl | 2.48; 3.79; 4.02(s, 3H); 6.52(s, 1H); 7.26–7.94(m, 8H) |
| 39 | 3-Phenyl-isoxazol-5-yl | 3.79; 4.02(s, 3H); 6.65(s, 2H); 7.32–7.88(m, 9H) |
| 40 | 5-(2-Methyl)phenyl-isoxazol-3-yl | 2.52; 3.79; 4.01(s, 3H), 6.55(s, 1H); 7.28–7.70(m, 8H) |
| 41 | 5-(1-tert.-Butoxy)ethylisoxazol-3-yl | 1.22(s, 9H); 1.47(d, 3H); 3.77; 3.96(s, 3H); 4.78(q, 1H); 6.31(s, 1H); 7.30–7.70(m, 4H) |
| 42 | 5-n-Propyl-isoxazol-3-yl | 0.99(t, 3H); 1.74(m, 2H); 2.73(t, 2H); 3.77; 3.97(s, 3H); 6.10(s, 1H); 7.28–7.68(m, 4H) |
| 43 | 5-(2-Acetyloxy)isopropyl-isoxazol-3-yl | 1.80(s, 6H); 2.04; 3.79; 3.97(s, 3H); 6.29(s, 1H); 7.28–7.70(m, 4H) |
| 44 | 5-Cyclooctyl-isoxazol-3-yl | 1.22–2.12(m, 15H); 3.77; 3.97 (s, 3H); 6.31(s, 1H); 7.30–7.70 (m, 4H) |
| 45 | 3-tert.-Butyl-isoxazol-5-yl | 1.34(s, 9H); 3.76; 4.01(s, 3H); |

TABLE I-continued

Ia

| No. | Het | Phys. data; H-NMR [δ, ppm], IR[cm⁻¹]; m.p. [°C.] |
|---|---|---|
| 46 | 3-Cyclohexyl-isoxazol-3-yl 5 | 6.26(s, 1H); 7.30–7.84(m, 4H) 1.26–2.81(m, 11H); 3.76; 4.01 (s, 3H); 6.20(s, 1H); 7.30–7.83 (m, 4H) |
| 47 | 5-α-Methoxybenzyl-isoxazol-3-yl | 3.43; 3.71; 3.91(s, 3H); 5.36; 6.30(s, 1H); 7.28–7.66(m, 9H) |
| 48 | 5-Cyclohexyl-1,3,4-thiadiazol-2-yl | 1.26–3.21(m, 11H); 3.81; 3.96 (s, 3H); 7.30–7.81(m, 4H) |
| 49 | 5-Phenyl-1,3,4-oxadiazol-2-yl | 160–161° C. |
| 50 | 5-(3-Methyl)phenyl-1,3,4-oxadiazol-2-yl | 166–167° C. |
| 51 | 5-(4-Cyano)phenyl-1,3,4-oxadiazol-2-yl | 188–189° C. |
| 52 | 5-(4-Chloro)phenyl-1,3,4-oxadiazol-2-yl | 161–162° C. |
| 53 | 5-(3,4,5-Trimethoxy)phenyl-1,3,4-oxadiazol-2-yl | 136–144° C. |
| 54 | 5-(5-Methyl)imidazol-4-yl-1,3,4-oxadiazol-2-yl | 198° C. (decomp.) |
| 55 | 5-Thien-2-yl-1,3,4-oxadiazol-2-yl | 196–197° C. |
| 56 | 5-Pyridin-3-yl-1,3,4-oxadiazol-2-yl | 168–170° C. |
| 57 | 5-Benzothien-2-yl-1,3,4-oxadiazol-2-yl | 209–213° C. |
| 58 | 5-(3-Chloro)benzothien-2-yl-1,3,4-oxadiazol-2-yl | 205–206° C. |
| 59 | 5-Furan-2-yl-1,3,4-oxadiazol-2-yl | 162–170° C. |
| 60 | 5-[(3-Methoxy-5-thien-2-yl)-phenyl]thien-2-yl | 3.68; 3.88; 4.04(s, 3H); 6.92–7.58(m, 12H) |

TABLE II

Ib

| No. | Het | Phys. data |
|---|---|---|
| 1 | Thiazol-2-yl | |
| 2 | Benzthiazol-2-yl | |
| 3 | Thien-2-yl | |
| 4 | Benzthien-2-yl | |
| 5 | Furan-2-yl | |
| 6 | Furan-3-yl | |
| 7 | Benzofuran-2-yl | |
| 8 | Benzofuran-3-yl | |
| 9 | Imidazol-2-yl | |
| 10 | Benzimidazol-2-yl | |
| 11 | Pyrrol-2-yl | |
| 12 | N-Methyl-pyrrol-2-yl | |
| 13 | Pyridin-2-yl | |
| 14 | Pyridin-3-yl | |
| 15 | Pyridin-4-yl | |
| 16 | Quinolin-2-yl | |
| 17 | 6-Chloropyridin-2-yl | |
| 18 | 4-Methyl-pyridin-2-yl | |
| 19 | Oxazol-2-yl | |
| 20 | Benzoxazol-2-yl | |
| 21 | 4-Phenyl-oxazol-2-yl | |
| 22 | 5-Phenyl-oxazol-2-yl | |
| 23 | 5-Methyl-isoxazol-3-yl | |
| 24 | 5-Bromomethyl-isoxazol-3-yl | |
| 25 | 5-Hydroxymethyl-isoxazol-3-yl | |
| 26 | 5-Acyloxymethyl-isoxazol-3-yl | |
| 27 | 5-(2-Methyl)phenyloxymethyl-isoxazol-3-yl | |
| 28 | 5-(2,5-Dimethyl)phenyloxy-methyl-isoxazol-3-yl | |
| 29 | 5-tert.-Butyl-isoxazol-3-yl | |
| 30 | 5-Cyclohexyl-isoxazol-3-yl | |
| 31 | 5-Pentyl-isoxazol-3-yl | |
| 32 | 5-[1-(4-Nitrophenoxy)ethyl]-isoxazol-3-yl | |
| 33 | 5-Benzoyloxymethyl-isoxazol-3-yl | |
| 34 | 5-β-Naphthyloxymethyl-isoxazol-3-yl | |
| 35 | 5-α-Naphthyloxymethyl-isoxazol-3-yl | |
| 36 | 5-Thiophenylmethyl-isoxazol-3-yl | |
| 37 | 5-Phenyl-isoxazol-3-yl | |
| 38 | 3-(2-Methyl)phenyl-isoxazol-5-yl | |
| 39 | 3-Phenyl-isoxazol-5-yl | |
| 40 | 5-(2-Methyl)phenyl-isoxazol-3-yl | |
| 41 | 5-(1-tert.-Butoxy)ethyl-isoxazol-3-yl | |
| 42 | 5-n-Propyl-isoxazol-3-yl | |
| 43 | 5-(2-Acetyloxy)isopropyl-isoxazol-3-yl | |
| 44 | 5-Cyclooctyl-isoxazol-3-yl | |
| 45 | 3-tert.-Butyl-isoxazol-5-yl | |
| 46 | 3-Cyclohexyl-isoxazol-5-yl | |
| 47 | 5-α-Methoxybenzyl-isoxazol-3-yl | |
| 48 | 5-Cyclohexyl-1,3,4-thiadiazol-2-yl | |
| 49 | 5-Phenyl-1,3,4-oxadiazol-2-yl | |
| 50 | 5-(3-Methyl)phenyl-1,3,4-oxadiazol-2-yl | |
| 51 | 5-(4-Cyano)phenyl-1,3,4-oxadiazol-2-yl | |
| 52 | 5-(4-Chloro)phenyl-1,3,4-oxadiazol-2-yl | |
| 53 | 5-(3,4,5-Trimethoxy)phenyl-1,3,4-oxadiazol-2-yl | |
| 54 | 5-(5-Methyl)imidazol-4-yl-1,3,4-oxadiazol-2-yl | |
| 55 | 5-Thien-2-yl-1,3,4-oxadiazol-2-yl | |
| 56 | 5-Pyridin-3-yl-1,3,4-oxadiazol-2-yl | |
| 57 | 5-Benzothien-2-yl-1,3,4-oxadiazol-2-yl | |
| 58 | 5-(3-Chloro)benzothien-2-yl-1,3,4-oxadiazol-2-yl | |
| 59 | 5-Furan-2-yl-1,3,4-oxadiazol-2-yl | |
| 60 | 5-[(3-Methoxy-5-thien-2-yl)phenyl]thien-2-yl | |

Use Examples

For the following use examples, the compounds used for comparison purposes were 2-(2-phenylphenyl)-glyoxylic acid methyl ester-O-methyloxium (A)—corresponds to EP-A 254 426—and methyl 2-(2-phenylphenyl)-3-methoxyacrylate (B)—disclosed in EP-A 178 826.

Use Example 1

Action on Plasmopara Viticola

Leaves of potted vines of the Müller-Thurgau variety were sprayed with aqueous suspensions containing (dry basis) 80% of active ingredient and 20% of emulsifier. To assess the duration of action, the plants were set up, after the sprayed-on layer had dried, for 8 days in the greenhouse. Then the leaves were infected with a zoospore suspension of Plasmopara viticola. The plants were first placed for 48 hours in a water vapor-saturated chamber at 24° C. and then in a greenhouse for 5 days at from 20° to 30° C. To accelerate and intensify the sporangiophore discharge, the plants ere then again placed in the moist chamber for 16 hours. The extent of fungus attack was then assessed on the undersides of the leaves.

The results show that compounds nos. 21, 32, 37, 38, 39, 40 and 45 from Table I, when employed as spray liquors containing 63 ppm of active ingredient, have a better fungicidal action (95%) than prior art active ingredients A and B (70%).

Use Example 2

Action on *Pyricularia oryzae* (Protective)

Leaves of pot-grown rice seedlings of the "TaiNong" variety were sprayed to runoff with aqueous emulsions containing (dry basis) 80% of active ingredient and 20% of emulsifier, and inoculated 24 hours later with an aqueous spore suspension of *Pyricularia oryzae*. The plants were then set up in climatic cabinets at 22° to 24° C. and 95 to 99% relative humidity. The extent of fungus attack was assessed after 6 days.

The results show that compounds nos. 29, 40, 41, 42, 43, 44, 45, 46 and 50, when applied as spray liquors containing 250 ppm of active ingredient, have a better fungicidal action (85%) than prior art active ingredient A (20%).

We claim:

1. A method of combatting insects, nematodes, or mites, comprising:

applying to insects, nematodes or mites, or their habitats, a pesticidally effective amount of a diaryl derivative of formula I:

U V W    I

Het

A

B where:

A is $=CHOR^1$, $=CHSR^1$, $=CHR^1$, $=CHCl$ or $=NOR^1$,

B is $OR^2$, $SR^2$ or $NR^2R^3$,

Het is a mono-, or dinuclear, five- or six-membered heterocylic structure which may carry from one to three radicals R, wherein R is halogen, nitro, cyano, $CO_2R^4$, $NR^4R^5$, $CONR^4R^5$, $S(O)_nR^4$ $P(O)(OR^4)_2$, substituted or unsubstituted $C_1-C_6$-alkyl, $C_1-C_4$-haloalkyl, substituted or unsubstituted $C_3-C_6$-cycloalkyl, $C_1-C_4$-alkoxy-$C_1-C_4$-alkyl, $C_1-C_4$-alkylthio-$C_1-C_4$-alkyl, substituted or unsubstituted $C_2-C_6$-alkenyl, substituted or unsubstituted $C_2-C_6$-alkynyl, $C_1-C_6$-alkoxy, $C_1-C_4$-thioalkoxy, substituted or unsubstituted benzylthio, $C_1-C_4$-alkylcarbonyl, substituted or unsubstituted phenylcarbonyl, substituted or unsubstituted aryl, substituted or unsubstituted aryloxy, substituted or unsubstituted arylthio, substituted or unsubstituted aryl-$C_1-C_4$-alkyl, substituted or unsubstituted aryl-$C_2-C_4$-alkenyl, substituted or unsubstituted aryl-$C_2-C_4$-alkynyl, substituted or unsubstituted aryloxy-$C_1-C_4$-alkyl, substituted or unsubstituted arylthio-$C_1-C_4$-alkyl, substituted or unsubstituted hetaryl, substituted or unsubstituted hetaryloxy, substituted or unsubstituted hetaryl-$C_1-C_4$-alkyl, substituted or unsubstituted hetaryl-$C_2-C_4$-alkenyl, substituted or unsubstituted hetaryloxy-$C_1-C_4$-alkyl, "substituted or unsubstituted" denoting the radicals halogen, cyano, nitro, $C_1-C_4$-alkyl, $C_1-C_4$-alkoxy, $C_1-C_4$-haloalkyl, $C_1-C_4$-haloalkoxy or $C_1-C_4$-alkoximino-$C_1-C_2$-alkyl and wherein n is 0, 1 or 2; $R^1$, $R^2$, $R^3$, $R^4$, $R^5$ are identical or different and each is hydrogen or $C_1-C_4$-alkyl; and U, V, W are identical or different and each is halogen, $C_1-C_4$-alkyl or $C_1-C_4$-alkoxy.

2. The method of claim 1, wherein A is $NOCH_3$, B is $OCH_3$, Het is isoxazolyl-3, R is 5-phenyl and U, V, W are hydrogen.

3. The method of claim 1, wherein A is $NOCH_3$, B is $OCH_3$, Het is isoxazolyl-5, R is 3-(2-methylphenyl) and U, V, W are hydrogen.

4. The method of claim 1, wherein A is $NOCH_3$, B is $OCH_3$, Het is 1,3,4-oxadiazolyl-2, R is 5-(3-methylphenyl) and U, V, W are hydrogen.

5. The method of claim 1, wherein A is $NOCH_3$, B is $OCH_3$, Het is thiazolyl-2 an U, V, W are hydrogen.

6. The method of claim 1, wherein A is $NOCH_3$, B is $OCH_3$, Het is 1,3,4-thiadiazolyl-2, R is 5-cyclohexyl and U, V, W are hydrogen.

7. The method of claim 1, wherein A is $NOCH_3$, B is $OCH_3$, Het is benzthiazolyl-2 and U, V, W are hydrogen.

8. The method of claim 1, wherein A is $NOCH_3$, B is $OCH_3$, Het is 5-(3-chloro)benzothien-2-yl-1,3,4-oxadiazol-2-yl and each of U, V and W is hydrogen.

9. The method of claim 1, wherein Het is isoxazolyl-3, isoxazolyl-5, 1,3,4-oxadiazolyl-2, thiazol-2, 1,3,4-thiadiazolyl-2 or benzthiazolyl-2.

10. The method of claim 1, wherein Het carries at least one radical R which is unsubstituted or substituted aryl or unsubstituted or substituted hetaryl.

11. The method of claim 1, wherein A is $=NOCH_3$.

12. The method of claim 1, wherein B is $—OCH_3$ or $—NHCH_3$.

* * * * *